(12) United States Patent　　(10) Patent No.: US 8,646,455 B2
Webster et al.　　(45) Date of Patent: *Feb. 11, 2014

(54) MANDIBULAR ADVANCEMENT DEVICE WITH POSITIVE POSITIONING HINGE

(75) Inventors: Daniel Webster, Shelburne, VT (US);
Larry Carlberg, Savage, MN (US);
Avery Lieberman, Tiburon, CA (US);
John Herald, Medina, OH (US)

(73) Assignee: Sleeping Well LLC, Shelburne, VT (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/454,710

(22) Filed: Apr. 24, 2012

(65) Prior Publication Data

US 2013/0098372 A1　　Apr. 25, 2013

Related U.S. Application Data

(63) Continuation-in-part of application No. 12/587,171, filed on Oct. 2, 2009, now Pat. No. 8,166,976.

(60) Provisional application No. 61/195,171, filed on Oct. 3, 2008.

(51) Int. Cl.
*A61F 5/56*　　(2006.01)
*A61C 5/14*　　(2006.01)

(52) U.S. Cl.
USPC ........... 128/848; 128/859; 128/861; 602/902; 433/6

(58) Field of Classification Search
USPC .......... 128/848, 859–862; 602/902; 433/6, 16
See application file for complete search history.

(56) References Cited

U.S. PATENT DOCUMENTS

| | | | | |
|---|---|---|---|---|
| 4,114,614 A * | 9/1978 | Kesling | .................... | 128/861 |
| 4,376,628 A * | 3/1983 | Aardse | .................... | 433/80 |
| 5,499,633 A * | 3/1996 | Fenton | .................... | 128/848 |
| 5,823,193 A * | 10/1998 | Singer et al. | .................... | 128/848 |
| 6,055,986 A * | 5/2000 | Meade | .................... | 128/848 |
| 6,129,084 A * | 10/2000 | Bergersen | .................... | 128/848 |
| 6,170,485 B1 * | 1/2001 | Orrico | .................... | 128/848 |
| 7,178,529 B2 * | 2/2007 | Kownacki | .................... | 128/848 |
| 8,166,976 B2 * | 5/2012 | Webster et al. | .................... | 128/848 |
| 8,534,289 B2 * | 9/2013 | Hernandez | .................... | 128/848 |

* cited by examiner

*Primary Examiner* — Patricia Bianco
*Assistant Examiner* — Kari Petrik
(74) *Attorney, Agent, or Firm* — Green Mountain Innovations; Alan Coté

(57) ABSTRACT

The invention is an oral appliance for prevention of sleeping problems including snoring, sleep apnea and bruxism, and may also be used to protect the teeth and gums from surgical instruments during surgery. Specifically, the appliance alters the position of the user's mandible, which is known as a method for reducing the restriction of the flow of air through the pharyngeal passageway. The appliance is a one-piece device molded from a flexible polymer. It includes an upper maxillary tray and a lower mandibulary tray. Both upper and lower trays include inner and outer walls which increase contact area with the teeth. The hinge mechanism of the device includes a positive positioning system comprised of opposed interlocking ridges. The ridges serve to create offset between the position of the upper tray and lower tray relative to each other, therefore advancing the user's mandible.

18 Claims, 11 Drawing Sheets

MANDIBULAR ADVANCEMENT DEVICE WITH POSITIVE POSITIONING HINGE

CROSS-REFERENCE TO RELATED APPLICATION

This application is filed as a Continuation-In-Part of U.S. patent application Ser. No. 12/587,171 filed Oct. 2, 2009, which claims the benefit of provisional patent application No. 61/195,171, filed Oct. 3, 2008

FEDERALLY-SPONSORED RESEARCH

None

SEQUENCE LISTING

None

FIELD OF THE INVENTION

The present invention relates to devices for prevention of sleeping problems including snoring and sleep apnea. Specifically, the device is an oral appliance which alters the position of the user's mandible. Advancing the position of the mandibular mouth structure relative to the position maxillary mouth structure is known as a method of reducing snoring and sleep apnea by reducing the restriction of the flow of air through the pharyngeal passageway. The decrease in air flow restriction causes a reduction in the vibration of soft tissue that's a cause of snoring, as well as reducing occlusion that's a cause of sleep apnea. In addition, the invention is used during surgical procedures to keep the airway (mouth) open, particularly while advancing the mandible. The advancement of the mandible prevents the collapse of the patient's airway, particularly for patients that suffer from Obstructive Sleep Apnea. It also serves to protect the teeth, gums, and related oral tissue from surgical instruments that may go in and out of a patient's mouth.

It is well-established that snoring and sleep apnea are sleeping problems that effect the quality of life of many people. Snoring is generally caused by the vibration of soft tissue and tongue against the back of the throat, which can be caused by restricted airflow through the pharyngeal passageway. Both the person snoring and other persons nearby can be affected by the resulting noise.

The relaxation of muscles during sleep can allow the structures and tissues of the nose and mouth to fall backwards against the back wall of the throat. While partial airflow restriction results in snoring, more complete obstruction can result in sleep apnea, also known as obstructive sleep apnea (OSA). OSA can result in the stoppage of breathing for short periods, which causes the sufferer to gasp for air, causing a change in the contraction of muscles and resulting significant disruptions in sleep patterns. With a lower quality of sleep, the sufferer may experience fatigue-induced problems such daytime sleepiness, depression, and other related problems. More severe complications such as heart attack or stroke can also be associated with decreased airflow and reduced blood-oxygen saturation levels.

Therefore, opening the pharyngeal passageway for increased airflow while sleeping can eliminate or significantly reduce snoring and OSA, and the resulting benefits are apparent.

Numerous methods for preventing snoring and/or OSA currently exist. One method is the advancement of the mandibular structure relative to the maxillary structure. It has been established since the 19$^{th}$ century that advancing the mandible results in increased airflow through the pharyngeal passageway. Thus advancement of the mandible while sleeping can reduce or eliminate snoring and/or OSA.

In an additional field of use, mouthpiece devices are used during surgical procedures both to keep the mouth and airway open, and to protect the teeth and oral tissues from any surgical instruments than may go in and out of a patient's mouth.

BACKGROUND

Description of Related Art

Numerous devices exist to advance the position of the mandible, and therefore prevent snoring and OSA. Such devices are in the form of a oral appliance worn by the user while sleeping. However, all such devices previously known face certain limitations. One common limitation is that custom molding is often required to shape the device to a user's teeth or mouth. This requires the expertise of a medical professional such as a dentist, and is therefore expensive and time-consuming. Additionally, many devices restrict the physiological movement of the user from freely opening and closing their jaw when the device is placed in the mouth. This is uncomfortable and unnatural for many users. The upper and lower trays of many devices force the jaw in a fixed, nearly closed, or closed position. A device which, by design, is not allowed to close completely would aid in the flow of air through the mouth.

U.S. Pat. No. 6,129,084 (Bergersen) describes an intra-oral device for advancing the user's mandible. The device is comprised of two u-shaped plates joined to form a hinge. The lower plate includes a channel. This lower plate channel has an inner wall (lingual wall), which faces the user's tongue, and an outer wall (labial-buccal wall), which faces the user's cheek and lips. Thus the user's mandibular teeth are cradled in the lower channel. The upper plate contains an outer wall (labial-buccal wall), but does not include an inner wall (lingual wall). The lack of an inner wall is to position the user's tongue in contact with the lingual side of the user's maxillary teeth, meaning the inside of the user's upper teeth. The preferred embodiment of this device is molded from pliable material in one piece and uses a simple hinge mechanism. The hinge is comprised simply of a thinning of the cross-section of the molded material, which allows the device to bend. It is described that the hinge may be sufficiently rigid to maintain a substantial gap in an open position, even when the user applies considerable force.

This '084 device, however, faces numerous limitations. The simple hinge mechanism is subject to wear as the pliable material is bent over many cycles of the user's mouth opening and closing. The mandibular advancement the device provides is created solely by the position of the hinge. Fatigue of the, material, compounded by a lack of mechanical reinforcement, may allow the simple living hinge to become sloppy and loose, rendering the device unable to properly advance the mandible. In addition, there's no mechanical element to prevent the device from completely closing, causing upper surface 24 and lower surface 14 to become co-planar.

U.S. Pat. No. 6,055,986 (Meade) describes a mandibular advancement mouthpiece that includes a hard shell that holds a soft, moldable material. The soft material rests against the teeth. The device is made in two major halves, an upper member and a lower member. One embodiment contains reciprocal surfaces 222 and 224 which fit together to fix the relative forward and backward positions of the upper and lower members to each other. However, with this device the upper and lower members are not connected or hinged to one another. Rather, this device relies on the material being molded to the user's individual teeth and the resulting contact adhesion in order to stay in place in the mouth.

U.S. Pat. No. 6,170,485 (Orrico) also describes system with two halves. It also uses moldable inner trays to interface with the teeth. It further describes tongues 30 and 32 which extend out of person's mouth. One tongue includes a plurality of holes 34, while the other tongue includes a projection 36. The projection aligns with one of the holes to create mandibular advancement, with different holes creating different amounts of advancement. However, with this device the upper and lower members are not connected or hinged to one another. Rather, this device relies on the material being molded to the user's individual teeth and the resulting contact adhesion in order to stay in place in the mouth.

U.S. Pat. No. 5,829,441 (Kidd) also describes system with two halves. It also uses moldable material to interface with the teeth. Means are included for adjustably advancing the user's mandible. However, this device requires the user to sleep with their jaw in a fixed, clenched position. Many people find sleeping with their jaw in a fixed position to be very uncomfortable, potentially even inhibiting sleep.

U.S. Pat. No. 6,516,805 (Thorton), as well as its related parent application, also describes a system with two halves. It also uses moldable material to interface with the teeth. A post 16 extends from the upper arch 12 and contacts the lower arch 14 to extend the user's mandible. However, this two-half design requires the post to be positioned at the front of the upper arch. Thus the post may disengage from the lower arch when the mouth is opened, causing the mandible to no longer be in an advanced position. In addition, there's no mechanical element to prevent the device from completely closing, causing upper arch and lower arch become co-planar.

U.S. Pat. No. 5,499,633 (Fenton) describes a system with two halves. It includes apertures 40 and projections 36. The projections are received into the apertures, therefore creating mandibular extension. However, with this device the upper and lower members are not securely connected or hinged to one another. The projections are made from the soft, moldable material of the rest of the device, and as such, may be difficult to engage in the apertures. In addition, the soft material of the projections may allow movement between the upper and lower members, thus not consistently advancing the mandible. In addition, the two members of the device may easily disengage from the teeth through the natural movement of the jaw. The device also requires boiling and molding.

U.S. Pat. No. 1,146,264 (Kelly) describes a dental splint. As best understood, this device use two separate trays to hold the jaw in position, with the trays apparently cemented to the user's teeth. This is used to create a static position if the bones of the jaw are fractured and must heal. It recites pillars 18, which hold the trays apart so that food may be inserted into the user's mouth.

U.S. Pat. No. 4,376,628 (Aardse) describes a tooth-treating mechanism in two halves It includes parallel ridges 9 and 10. The ridges serve to center one device half over the other device half. The orientation of the ridges does not create mandibular advancement, as they are in a direction perpendicular to that required for mandibular advancement.

CA 2,177,284 (Voss) describes a one-piece mandibular advancement device. This device is molded from pliable material in one piece and uses a simple hinge mechanism. The hinges 4 and 4' are comprised of a thinned cross-section of the molded material, in conjunction with half-cylinder 40 and notch 41. This assembly allows the device to bend. This device, however, faces numerous limitations. The simple hinge mechanism is subject to wear as the pliable material is bent over many cycles of the user's mouth opening and closing. The mandibular advancement the device provides is created solely by the position of the hinge, and faces similar limitations to the device described in '084 (Bergersen) In addition, there's no mechanical element to prevent the device from completely closing, causing upper surface 24 and lower surface 14 to become co-planar and therefore restricting airflow through the mouth.

Other manibular devices are disclosed in patents and in the marketplace as well. However, all face similar limitations as the above described inventions. In summary, many of the above devices require fitting, molding, or adjustment by a dental professional and fabrication laboratory. This process is costly and time-consuming, and prevents by non-skilled persons using the device straight-out-of-the-package. Still other systems use a simple hinge that quickly wears and may no longer properly advance the mandible. Many of these devices also restrict the user from opening his/her mouth, which many users find undesirable.

Various mouthpiece devices also exist for use during surgery as well, such as 5,794,627 to Frantz; 4,305,709 to Bruhn; 8,104,467 to NaPier; 3,513,838 to Foderick, and others.

BRIEF SUMMARY OF THE INVENTION

Several objects and advantages of the present invention will be made clear. What is needed is a mandibular advancement device that does not require fitting, heating, molding, or adjustment in order to be used. Additionally, a device is needed that's durable, easy to wear, and simple to use. It should be comfortable and allow the user to freely open and close his/her mouth so that natural jaw movement is not inhibited. Further, there's a need for a device that can be used straight-out-of-the-package by non-skilled persons, eliminating the need for costly, time-consuming fitting by a dental professional and fabrication laboratory.

In the preferred embodiment of the invention, a one-piece device is molded from a flexible thermoplastic elastomer such as Kraton®. The device includes an upper maxillary tray and a lower mandibulary tray connected by a hinging mechanism. Both upper and lower trays include inner and outer walls which increase contact area with the teeth. The lingual surface of the mandibulary tray features a flange which extends down into the lingual vestibule to provide greater contact surface to advance the mandible. The flange is designed to be of a length which extends into the lingual vestibule but does not contact the lingual frenulum.

The hinge mechanism of the preferred embodiment includes a positive positioning system comprised of opposed interlocking ridges. The ridges serve to create and maintain offset between the position of the upper tray and lower tray relative to each other, therefore advancing the user's mandible. The location of the ridges, close to the hinge points, is also advantageous because the ridges continue to engage one another and therefore advance the mandible even when the jaw is almost entirely open. Further, the ridges are self-aligning and easily engage with virtually no chance of jamming.

The preferred embodiment also includes posts located near the front of the upper tray and the lower tray. These posts create an air gap that prevents the upper tray and lower tray from completely closing against one another. The preferred embodiment is also contoured and curved to comfortably fit in the mouth and on the teeth. Related to the contouring is a cleft notch on the upper front of the maxillary tray to avoid rubbing and irritation to the connective tissue (maxillary labial frenulum) on the inside of the upper lip.

In addition, the device may be made with different amount of offset, to create different amounts of mandibular advancement. The preferred range of offset varies between 0 mm and 10 mm, though amounts greater than this are possible.

While all of the above features of the device are useful for mandibular advancement while sleeping, the device also can be used during surgical procedures, by serving to keep the airway open, protect the teeth and oral tissue from surgical instruments placed into the mouth, and optionally to advance the mandible.

DESCRIPTION OF THE REFERENCE NUMERALS 10 overall device
12 upper maxillary tray
14 lower mandibulary tray
16a inner wall of upper maxillary tray
16b outer wall of upper maxillary tray
18a inner wall of lower mandibulary tray
18b outer wall of lower mandibulary tray
18c lingual flange portion of inner wall of lower mandibulary tray
20a right post
20b left post
21a right retention post
21b left retention post
22a overall hinge right
22b overall hinge left
24a forward upper interlocking ridge right
24b aft upper interlocking ridge right
24c lower interlocking ridge right
26a forward upper interlocking ridge left
26b aft upper interlocking ridge left
26c lower interlocking ridge left
28a flexible hinge section right
28b flexible hinge section left
32 outer tray wall chamfer
34 curved contour of upper maxillary tray
36 curved contour of lower mandibulary tray
38 cleft contour
40 tooth retention tab

DETAILED DESCRIPTION

In all figures, the device is shown in the open position, when not in the user's mouth.

Figure 1:
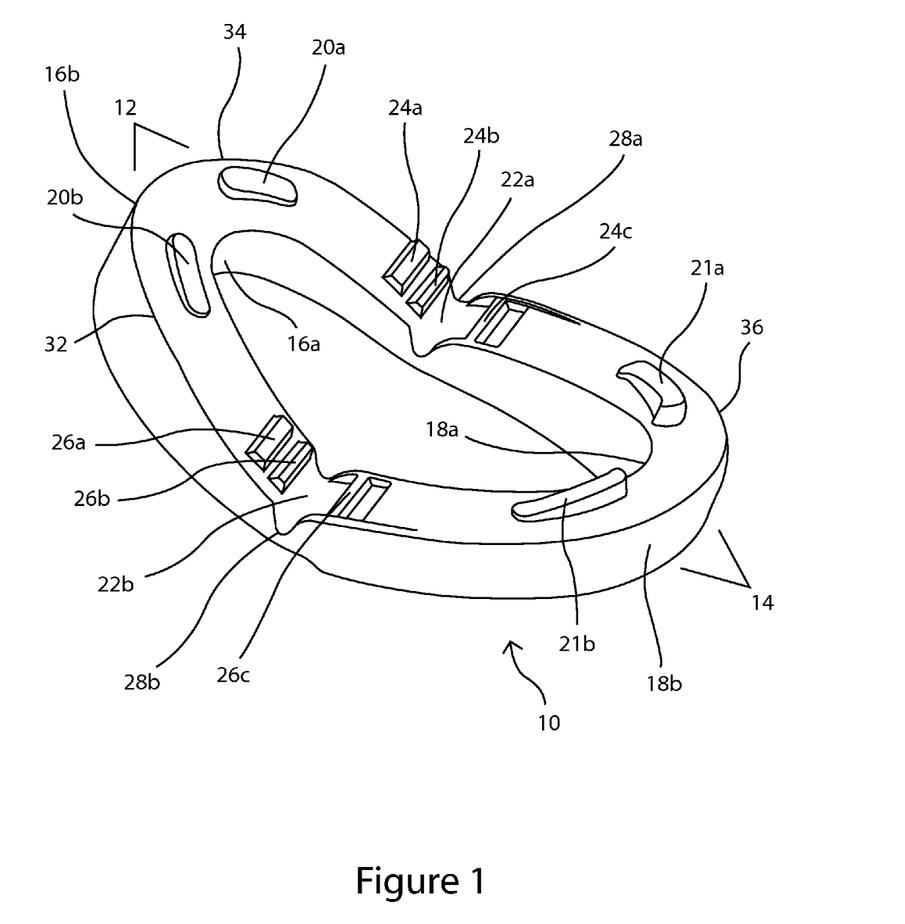
FIG. 1 is a perspective view of the device in the open position, when not in the user's mouth

FIG. 1 is a perspective view of the preferred embodiment of the invention. As can be seen, the one-piece overall device 10 folds at overall hinge right 22a, and overall hinge left 22b. Upper maxillary tray 12 and lower mandibulary tray 14 are both u-shaped, joined together by hinges 22a and 22b. The length of the upper and lower trays are preferably designed so that the device extends back to the centers of the upper first molars when fully inserted. This allows for ample contact between the trays and the teeth to maintain device postioning, but doesn't extend too far into the mouth so as to create discomfort or promote gagging.

FIG. 1 also shows the interlocking ridges of each hinge. Forward upper interlocking ridge right 24a, aft upper interlocking ridge right 24b, lower interlocking ridge right 24c, together form the positive engagement system. The preferred embodiment uses ridges that are trapezoidal in cross-section. This shape creates a chamfered profile that easily lets lower ridge 24c mesh with upper ridges 24a and 24b as the device is closed. This is identical for the left side hinge 22b. The molded material is thinnest in cross-section on the overall device at flexible hinge section right 28a and flexible hinge section left 28b. The thinned cross-section permits the device to flex and bend as a hinge. The hinge also acts as a low-force spring, with the force of the springs aiding to keep the upper tray 12 in contact with the user's maxillary teeth, and lower tray 14 in contact with the user's the mandibulary teeth. As is seen in FIG. 1, the ridges are substantially parallel to the hinging axis.

FIG. 1 also shows right post 20a and left post 20b. These posts prevent upper maxillary tray 12 and lower mandibulary tray 14 from closing against each other completely. Of course, said posts could be placed elsewhere on the device, such as an identical location on tray 14. Posts 20a and 20b may be located in different positions on either tray, however the location shown offers advantages of being further ideally located to maintain airflow. Right retention post 21a and left retention post 21b serve similar function to posts 20a and 20b. All posts further serve by: providing additional support for their respective tray, minimizing flex and bending for their respective tray, and correcting overall angulation as each post contacts its opposing tray.

Figure 2A:
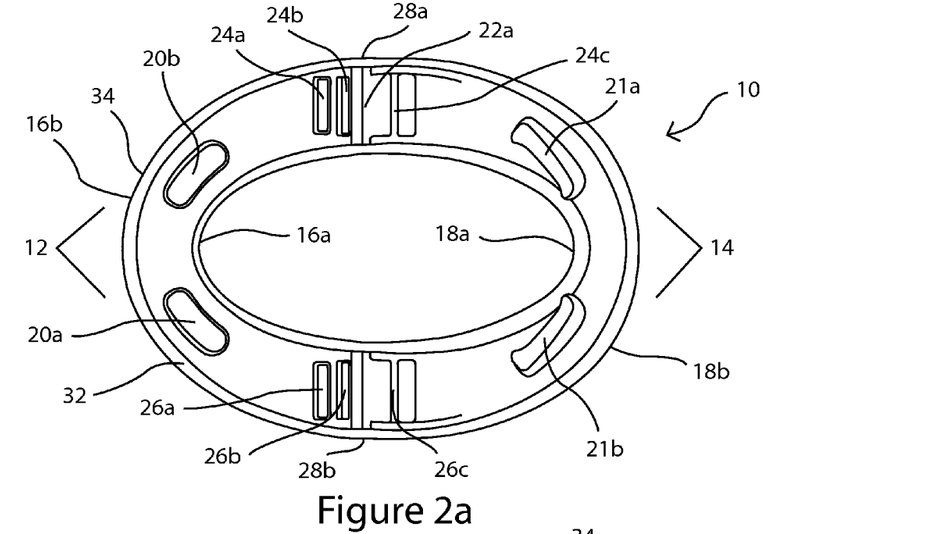
FIG. 2a is a top view of the device

FIG. 2a is a top view of the device, further showing the locations of the all of the interlocking ridges, as well as all posts.

Figure 2B:
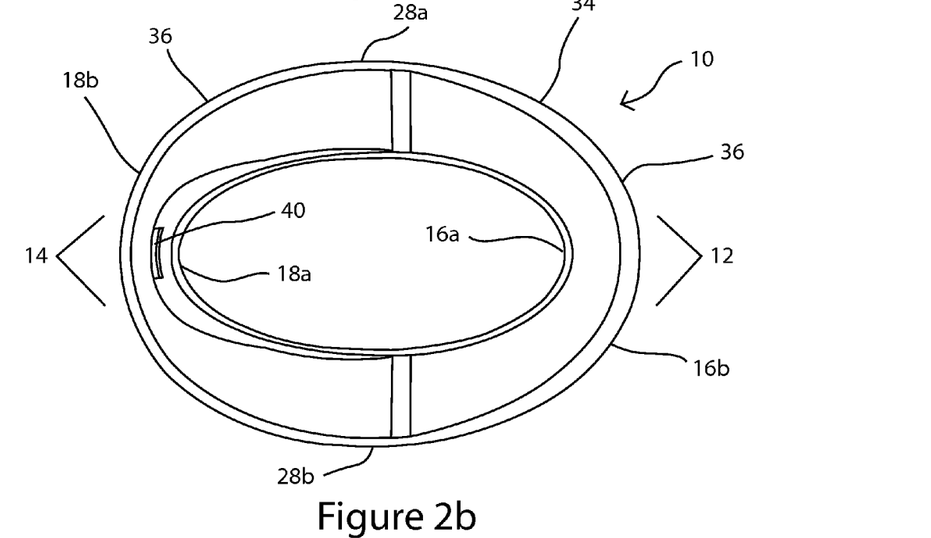
FIG. 2b is a bottom view of the device

FIG. 2b is a bottom view of the device, further showing the tooth retention tab 40.

Figure 3A:
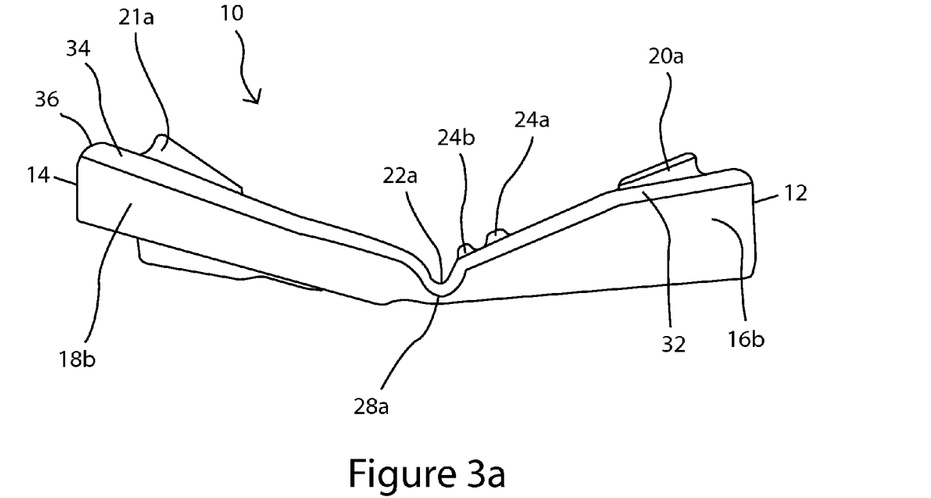
FIG. 3a is a right side view of the device

FIG. 3a is a right side view of the device, further showing the locations of one side of interlocking ridges, as well as posts. Also seen is the outer wall of upper maxillary tray 16b, inner wall of lower mandibulary tray 18a, and outer wall of lower mandibulary tray 18b. Outer tray wall chamfer 32, curved contour of upper maxillary tray 34, and curved contour of lower mandibulary tray 36 are all also apparent. 18c shows the ligual flange portion of the inner wall of the lower mandibulary tray. The flange 18c serves to extend into the user's lingual vestibule to provide greater contact surface for advancing the mandible.

Figure 3B:
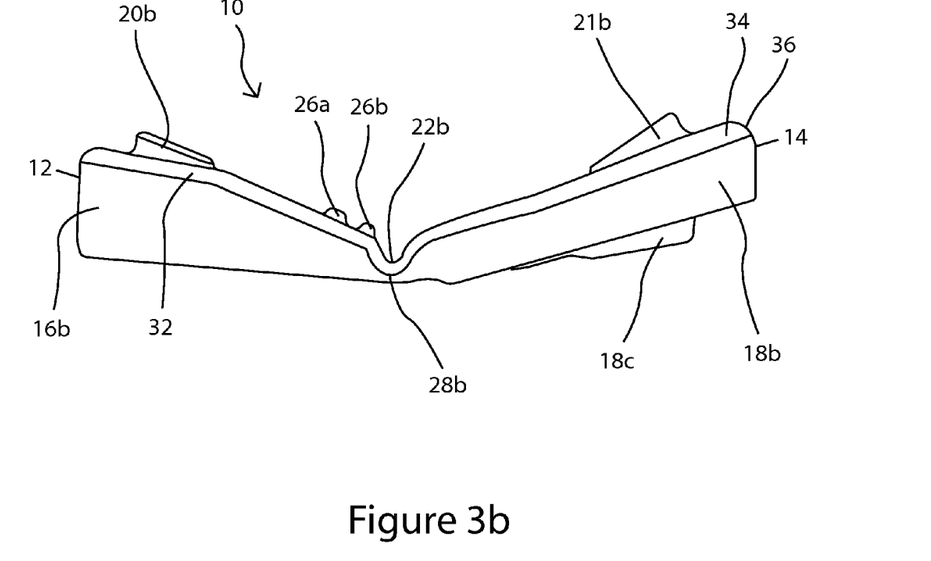
FIG. 3b is a left side view of the device

FIG. 3b is a left-side view of the device, showing similar features to view 3a

Figure 4A:
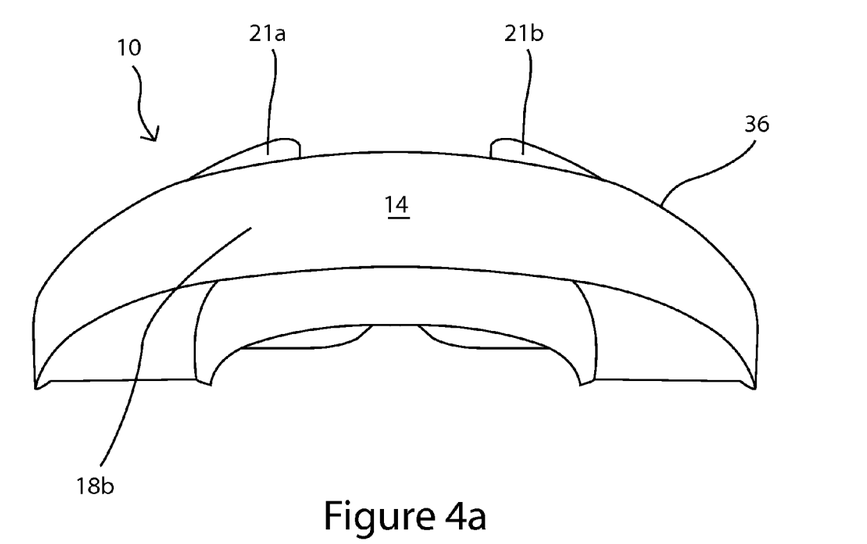
FIG. 4a is a back-end view of the device

FIG. 4a is a view from the back-end of device.

Figure 4B:
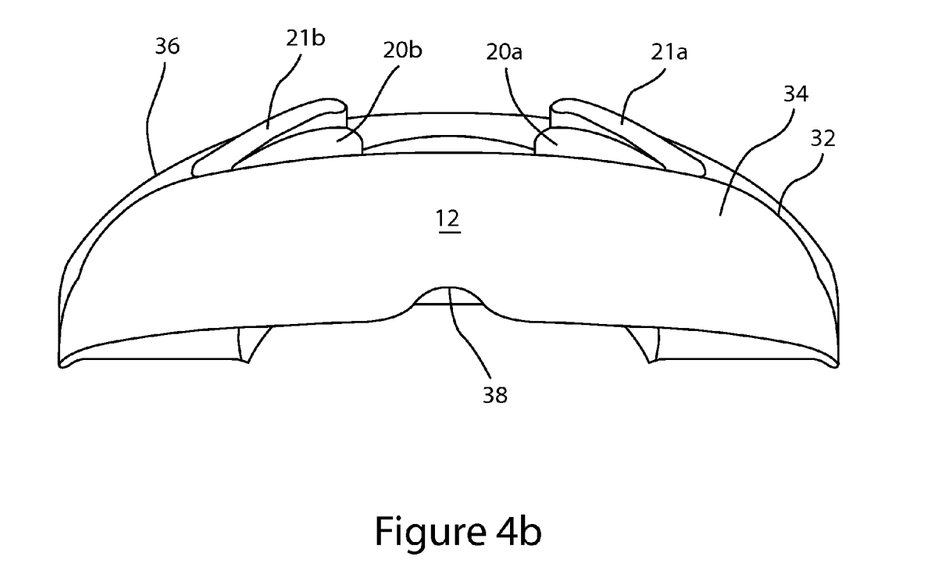
FIG. 4b is a front-end view of the device

FIG. 4b is a view from the front-end of device. Cleft contour 38 is visible in this view.

Figure 5:
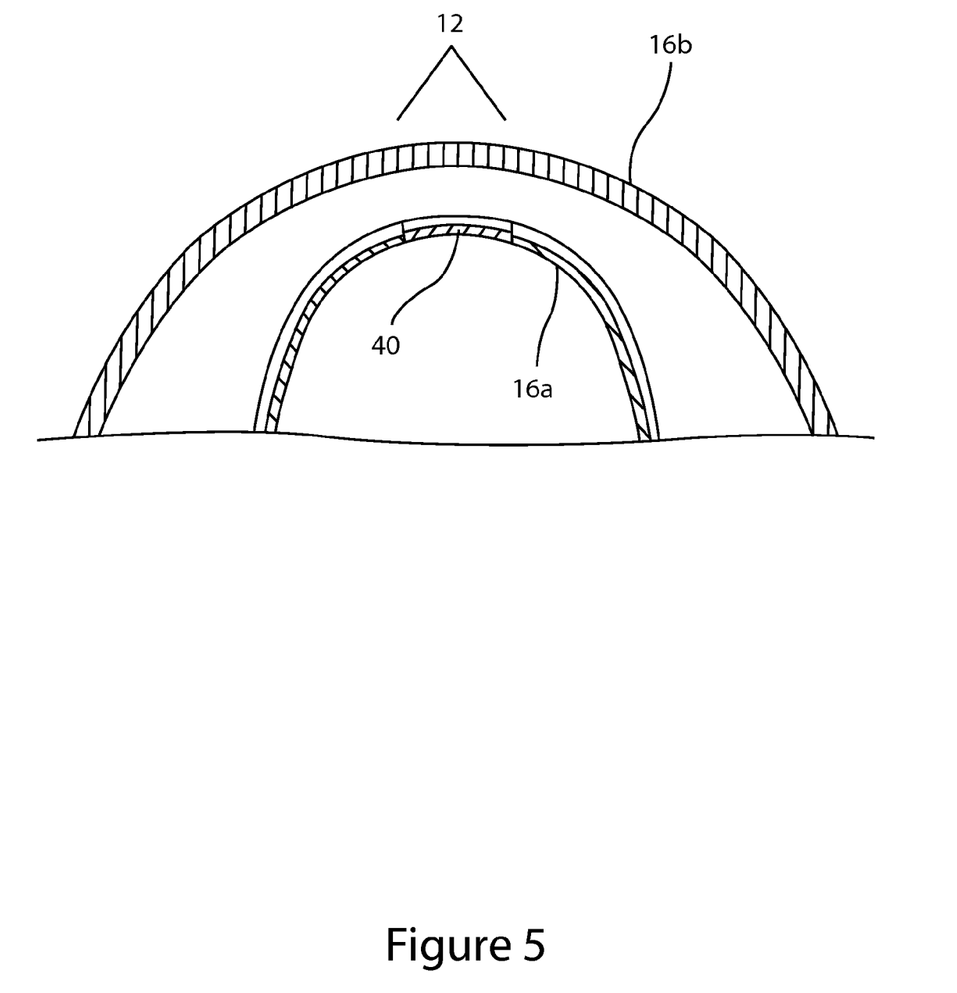
FIG. 5 is a bottom view of the front section of the lower tray of the device

FIG. 5 is a bottom view of the front section of the lower tray of the device. In this view, tooth retention tab 40 is visible.

Figure 6:
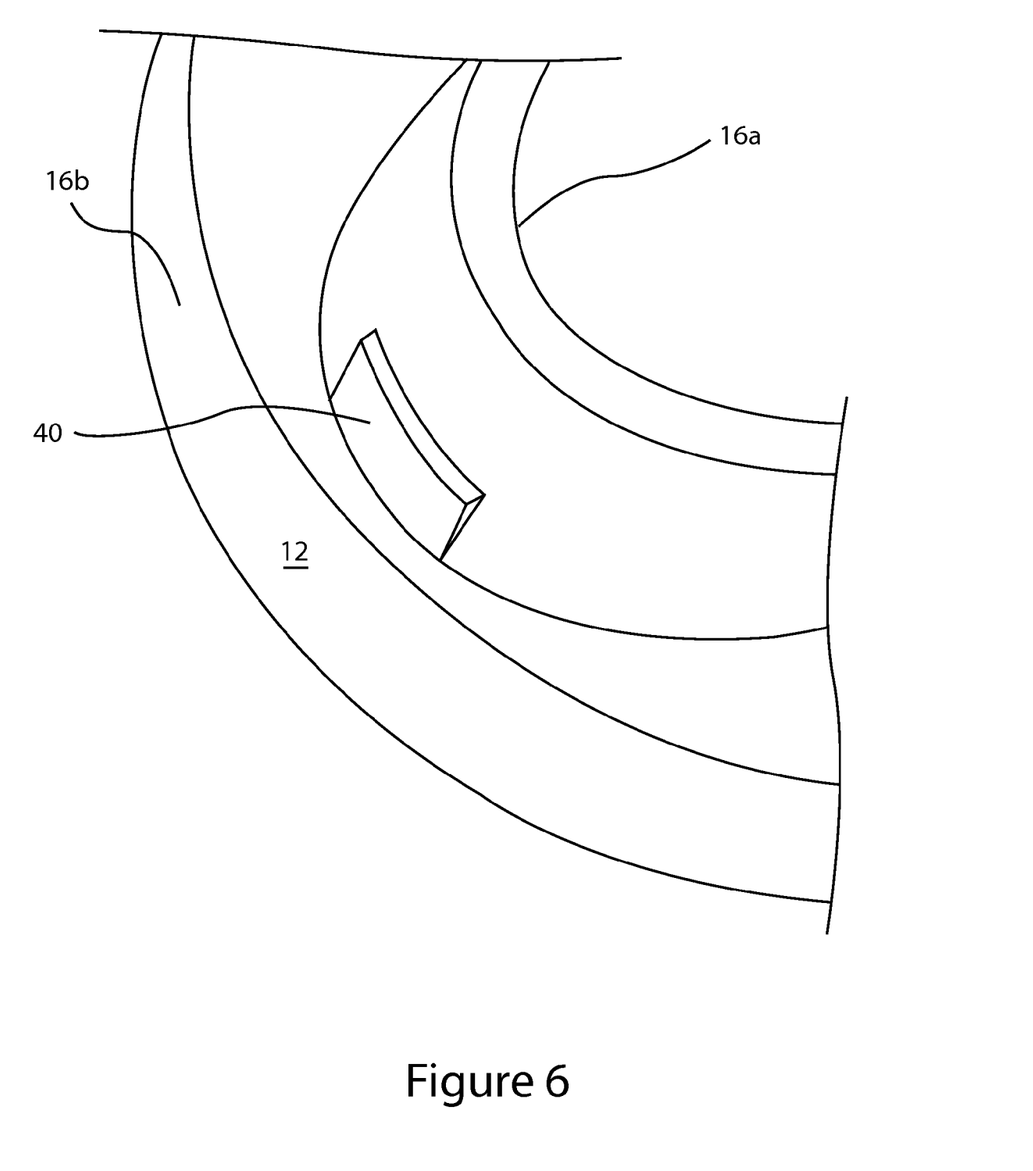
FIG. 6 is a perspective view of the front section of the lower tray of the device
Figure 7:
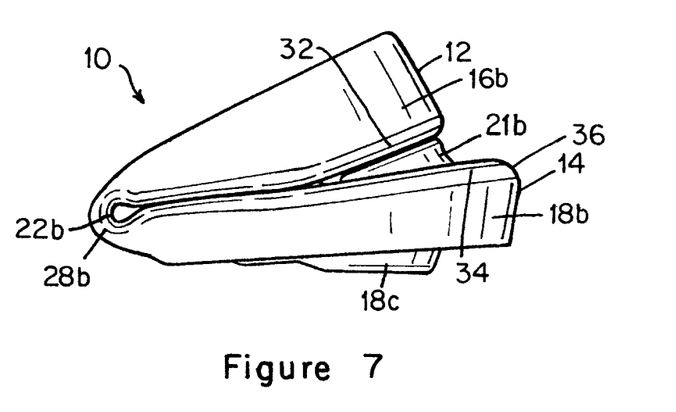
FIG. 7 is a side view of the device in its closed position, as it would be placed in a user's mouth.
Figure 8:
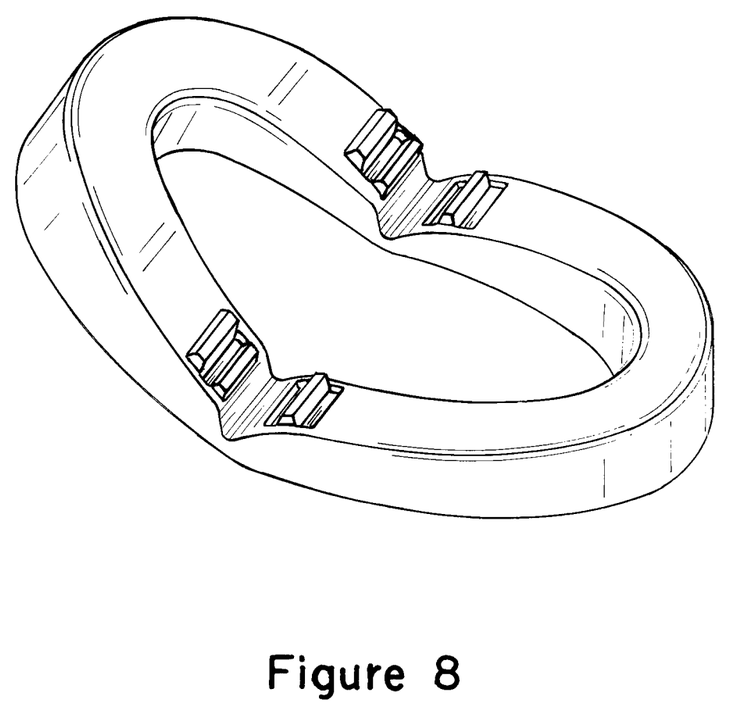
FIG. 8 is a perspective view of an alternate embodiment of the device in the open position, when not in the user's mouth
Figure 9:
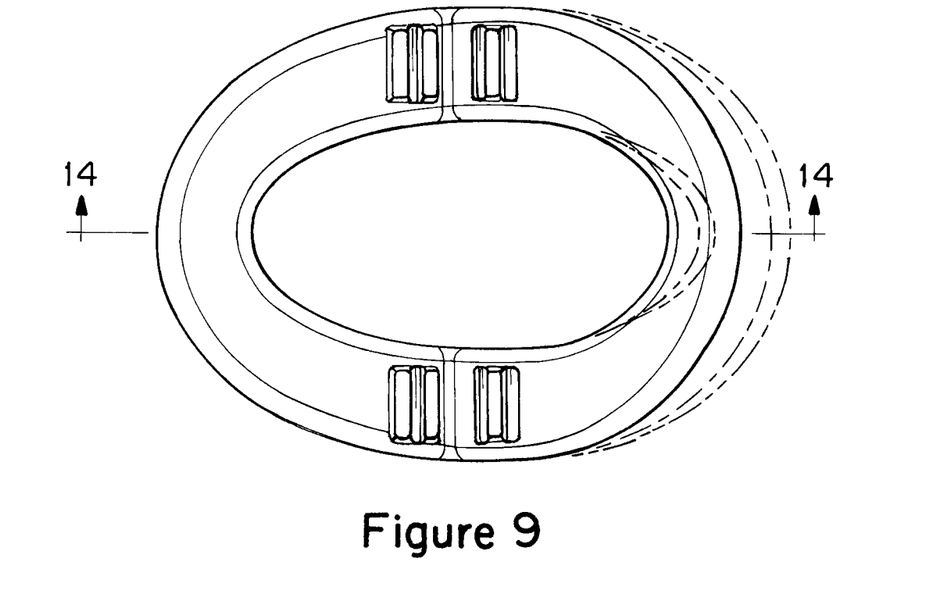
FIG. 9 is a top view of an alternate embodiment of the device
Figure 10:
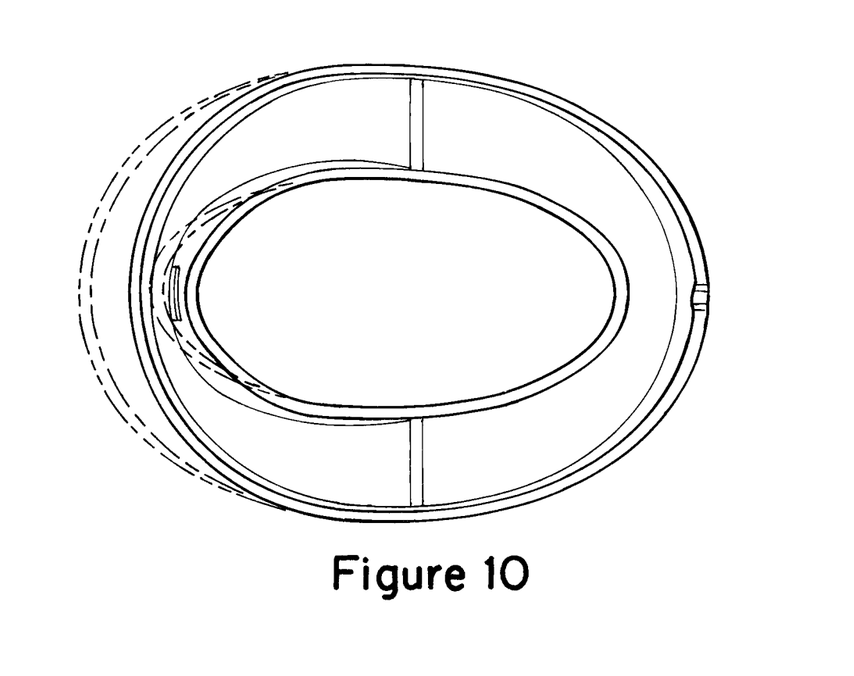
FIG. 10 is a bottom view of an alternate embodiment of the device

FIG. 6 is a perspective view of the front section of the lower tray of the device. In this view, tooth retention tab 40 is visible.

Overall device 10 readily bends in half at hinges 22a and 22b. It is then inserted into the user's mouth, with the user's maxillary teeth pressing into upper maxillary tray 12 and the user's mandibular teeth pressing into lower mandibulary tray 14. The user's maxillary teeth are cradled by the inner wall of upper maxillary tray 16a and the outer wall of upper maxillary tray 16b. The user's mandibular teeth are contacted by the inner wall 18a of lower mandibulary tray 14, and in addition, the outer wall 18b of the tray 14 may contact the maxillary teeth. The opposing forces of the contact with the facial surface of the upper maxilliary dentition and in particular the contact of the inner flange of tray 18a to the lingual surface of the lower lingual dentition maintain the mandible in a forward position relative to the maxilla, whereby the airway passage in the nasopharynx, oropharynx and laryngopharynx are kept substantially free of occlusion, thus reducing or eliminating snoring and/or OSA.

The position of the two trays relative to each other, or offset, is determined by the location of overall hinges 22a and 22b. The offset is further reinforced by the pairs of hinged ridges, 24a, 24b, 24c, and 26a, 26b, 26c. At the device bends and is placed in the user's mouth, the ridged hinges engage and further reinforce the offset. The ridges continue to engage as a user partially or even fully opens his/her mouth. The location of the ridges, close to the hinge point, allows the ridges to stay engaged over a wider range of mouth motion than if the ridges were located closer to the front of the overall device. It is therefore advantageous to incorporate the ridges into the hinge portion of the overall device. Further, the interlocking ridges help prevent side to side and rotational motion between the upper and lower trays, thereby maintaining alignment.

In the preferred embodiment, the right and left lower interlocking ridges, 24c and 26c respectively, may be formed such that the highest point of each ridge is co-planar with the larger planar surface of lower mandibulary tray 14. This effectively creates a small recess for each ridge, 22a and 22b, to engage into, thereby creating a more positive engagement which helps insure the desired mandibular advancement is achieved. Alternately, ridges 24c and 26c may be more simply formed such that they are raised above the planer surface of tray 14.

While the preferred embodiment shows a one-piece, living-hinge design, other types of hinges designs could be employed as well. In alternate embodiments, the upper and lower trays could be made as separate pieces and joined together by separate hinge pieces. Alternatively the hinging mechanism could be made of the same or completely different type of material including but not limited to alloy, metal, plastic, polyethelene, etc. In referring to the upper tray to the lower tray being connected, the method may be to connect the two pieces by molding them together in one continuous piece with a resulting living hinge, or by connecting separate pieces joined with separate hinges.

Another inventive element of the preferred embodiment are the two airflow posts 20a and 20b located near the front of the upper maxillary tray 12. These posts create an air gap that prevents the planar surfaces of the upper tray 12 and lower tray 14 from completely closing against one another. This insures air will flow through the user's mouth, even if the teeth are tightly clenched during sleep.

In the alternate embodiment of the invention, as seen in FIGS. 8-17, these airflow posts are not included. As the preferred use for the alternate embodiment is during surgery, omission of the posts creates a smooth surface to the upper and lower trays that will not interfere with surgical instruments. Here, surgical instruments includes any type of device that may enter into or pass through a patient's mouth for any period of time, such as handheld instruments, anesthesiology equipment, breathing tubes, and other similar devices.

Optionally, right retention post 21a and left retention post 21b may be included. Posts 21a and 21b are shown on lower mandibulary tray 14. When the inventive device is placed in the closed position in the user's mouth, posts 21a and 21b help insure that the mandible stays in an advanced position by engaging against posts 20a and 20b and thereby further preventing lower tray 14 from moving backward relative to upper tray 12.

Another inventive element which may be optionally included is tooth retention tab 40. This tab is located on the inner wall of the lower mandibulary tray 14, in the location seen in FIG. 6 and FIG. 5. This tab is positioned and shaped such that it interfaces with the lingual surface of the mandibular central incisors. The naturally curved lingual surface of the mandibular central incisors mates with the retention tab, which helps keep the lower mandibulary tray positioned on the teeth and helps prevents the tray from sliding off and disengaging with the teeth.

The preferred embodiment is also contoured and curved to comfortably fit in the mouth and on the teeth. The edge of both the upper and lower trays are chamfered, or otherwise made non-sharp, to be comfortable in the user's mouth. Related to the contouring is cleft contour 38 on the upper front of the maxillary tray 12 to avoid rubbing and irritation to the connective tissue on the inside of the upper lip. Likewise, the wall thickness of the device may vary throughout to create an optimal shape for comfort while maintaining durability.

In the preferred embodiment, the device is molded from an appropriate material such as Kraton® polymer. Kraton® polymers provide additional comfort and cushion to the user. The rubbery properties of the polymer increase the amount of surface tension and contact adhesion with the teeth and prevent the device from falling out during use. Kraton® polymers will also wear longer and better than the traditional resins currently on the market. Of course, other suitable materials could be employed as well, whether in the form of synthetic polymers or even natural rubber.

While the overall device serves primarily for the purpose of mandibular advancement, with the associated sleep-related benefits, the device also serves to reduce problems associated with bruxism, or the grinding of the teeth. The mechanism for this is readily apparent, as the upper and lower trays prevent the maxillary and mandibular teeth from making direct contact.

In addition, an alternate embodiment, as shown in FIGS. 8, 9, 10, 11, 12, 13, 14, 15, 16, is optimized for use in surgical applications. This embodiment omits airflow posts as described above.

Figure 11:
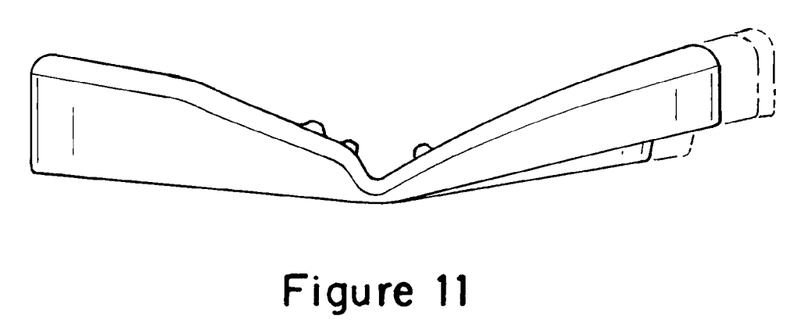
FIG. 11 is a right side view of an alternate embodiment of the device, with phantom lines representing other embodiments with great amounts of offset
Figure 12:
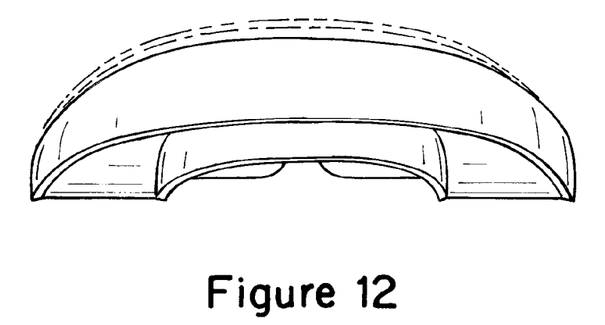
FIG. 12 is a back-end view of an alternate embodiment of the device, with phantom lines representing other embodiments with great amounts of offset
Figure 13:
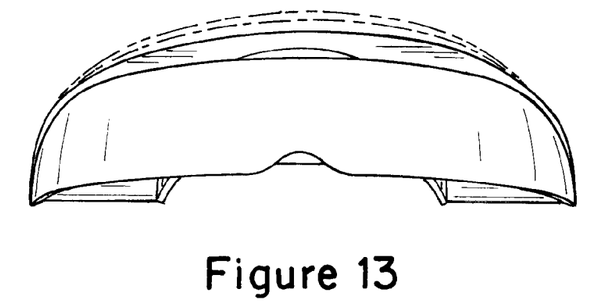
FIG. 13 is a front-end view of an alternate embodiment of the device, with phantom lines representing other embodiments with great amounts of offset
Figure 14:
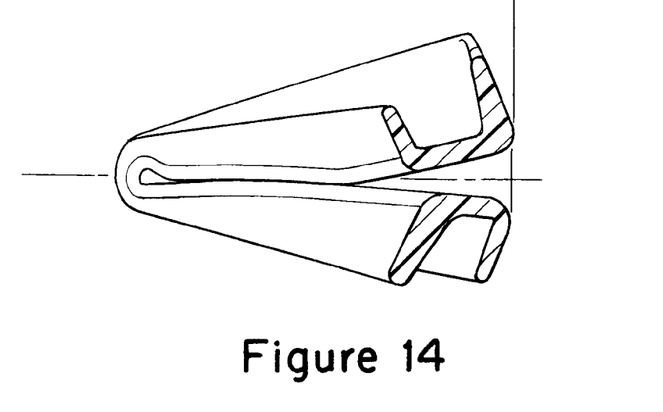
FIGS. 14-16 are cross sectional views (see FIG. 9 for reference) of the device in a closed position, as it would be placed in a user's mouth, which each FIG. 14, 15, 16 representing embodiments with different amounts of offset
Figure 15:
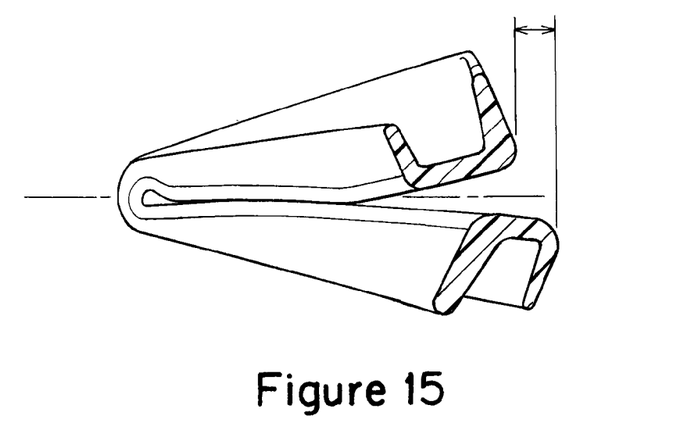
Figure 16:
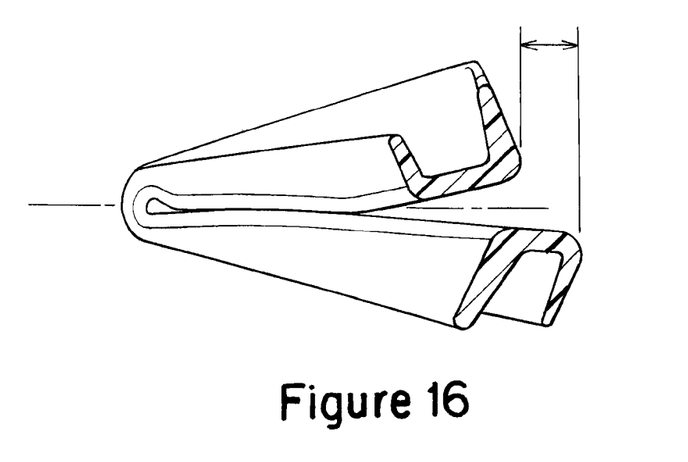

In either embodiment shown, the amount of offset created between the upper and lower trays may vary. This is illustrated in several figures, with FIG. 11 showing an example of three different amounts of offset. For some applications, surgical in particular, there may be occasions for 0 mm of offset between the trays, as shown in the cross section of FIG. 14. FIG. 15 shows incrementally more offset, with FIG. 16 showing even greater offset.

The preferred range of offset varies between 0 mm and 10 mm, though amounts greater than this are possible. A range products made be made, each with a different offset. For example, product 1 with 0 mm of offset, product 2 with 2 mm offset, product 3 with 4 mm of offset, and so on. A product with the correct amount of offset can be chosen by either the end user or by a medical professional, or a combination thereof.

For surgical use, the device's advantages, such as staying in place on both the maxillary and mandibular teeth and keeping the airway open, are readily apparent. The device may also create mandibular advancement during surgery, with advancement serving to keep the airway open and prevents the collapse of the airway.

The above described elements combine to create a mandibular advancement device that does not require custom fitting and is easily used off-the-shelf. Although the above specification and related drawings describe a specific embodiment of the invention, this should not be interpreted as limiting the scope of the invention to these particular elements. The interpretation of the scope of the invention should be determined by the claims and their legal equivalents.

What is claimed:

1. A mouthpiece device comprising:
   an upper maxillary tray, said upper tray including an inner wall and an outer wall;
   a lower mandibulary tray, said lower tray including an inner wall and an outer wall;
   two hinge mechanisms which pivotably connect on an axis said upper tray's rearmost portion to said lower tray's rearmost portion;
   and interlocking ridges in said hinge mechanisms to further engage said lower tray with said upper tray, said interlocking ridges positioned on said upper tray's and said lower tray's rearmost portions immediately in front of said axis.

2. The device of claim 1 which further serves to protect teeth and oral tissue from surgical instruments placed into a user's mouth during surgery.

3. The device of claim 1 in which said hinge mechanisms are positioned to create offset between said upper tray and said lower tray when said upper tray and said lower tray are pivoted about said axis.

4. The device of claim 3 in which said offset measures between 0 and 10 mm.

5. The device of claim 1 in which the interlocking ridges are substantially parallel to said axis that connects said upper tray to said lower tray.

6. The device of claim 1 which further includes a cleft contour on said upper tray.

7. The device of claim 1 which further includes a tooth retention tab on said inner wall of said lower tray.

8. The device of claim 1 in which said hinge mechanisms further function as springs, with said springs' force aiding to keep said upper tray in contact with a user's maxillary teeth and said lower tray in contact with said user's mandibular teeth.

9. The device of claim 1 in which said inner wall of said lower tray includes a flange portion, such that in use said flange extends into a user's lingual vestibule to provide greater contact surface for advancing said user's mandible.

10. The device of claim 1 in which said upper tray and said lower tray extend to the centers of a user's upper first molars when said device is fully inserted.

11. The device of claim 1 which further serves to reduce effects of bruxism.

12. A method of engaging a mouthpiece and teeth together, comprising:
    engaging a user's maxillary teeth with an upper maxillary tray, said upper tray including an inner wall and an outer wall;
    engaging said user's mandibular teeth with a lower mandibulary tray, said lower tray including an inner wall and an outer wall;
    connecting, on an axis, said upper tray's rearmost portion to said lower tray's rearmost portion with hinge mechanisms;
    further connecting said upper tray and said lower tray together with interlocking ridges, said interlocking ridges positioned on said upper tray's and said lower tray's rearmost portions immediately in front of said axis.

13. The method of claim 12 which further protects teeth and oral tissue from surgical instruments placed into a user's mouth during surgery.

14. The method of claim 12 in which said hinge mechanisms are positioned to create offset between said upper tray and said lower tray when said upper tray and said lower tray are pivoted about said axis.

15. The method of claim 12 in which said offset measures between 0 and 10 mm.

16. The method of claim 12 in which the interlocking ridges are substantially parallel to said axis that connects said upper tray to said lower tray.

17. The method of claim 12 in which said hinge mechanisms further function as springs, with said springs' force aiding to keep said upper tray in contact with a user's maxillary teeth and said lower tray in contact with said user's mandibular teeth.

18. The method of claim 12 which further serves to reduce effects of bruxism.

* * * * *